United States Patent [19]

Bolduc et al.

[11] 4,119,098

[45] * Oct. 10, 1978

[54] MATERIAL DISPENSING APPARATUS

[75] Inventors: Lee R. Bolduc, St. Louis Park; Eugene A. Dickhudt, St. Paul, both of Minn.

[73] Assignee: Population Research Incorporated, Clearwater, Fla.

[ * ] Notice: The portion of the term of this patent subsequent to Jul. 9, 1991, has been disclaimed.

[21] Appl. No.: 757,780

[22] Filed: Jan. 10, 1977

[51] Int. Cl.² .............................................. A61M 1/00
[52] U.S. Cl. .................................... 128/235; 128/1 R
[58] Field of Search ............... 128/260, 235, 234, 1 R, 128/232, 349 B, 240, 241, 246, 127, 224

[56] References Cited

U.S. PATENT DOCUMENTS

| | | | |
|---|---|---|---|
| 3,822,702 | 7/1974 | Bolduc et al. | 128/235 |
| 3,871,374 | 3/1975 | Bolduc et al. | 128/235 |
| 3,875,939 | 4/1975 | Bolduc et al. | 128/235 |

Primary Examiner—John D. Yasko
Attorney, Agent, or Firm—Lew Schwartz; Joseph F. Breimayer; Wayne A. Sivertson

[57] ABSTRACT

A dispensing apparatus for placing a settable, fluid-like material in the uterine cavity and moving the material from the uterine cavity into the Fallopian tubes of a female. An elongated probe carries an expandable member, and a housing connected to the probe has a piston and cylinder structure and a container for storing the material. Material and expansion drive mechanisms are connected to an actuator selectively controlled by an operator. By operating the actuator or control means, the operator causes the material to be dispensed into the uterine cavity while at the same time sealing the cervical entrance to the cavity, and causing the expansion means to fully expand to conform to the shape of the uterine cavity and force the dispensed materials into the canals of the Fallopian tubes. By maintaining actuation of the control means, the operator causes the expandable member to substantially seal the isthmus, that is, the entrance from the uterine cavity into the Fallopian tubes, thus preventing the dispensed materials from flowing through the canals of the Fallopian tubes and allowing them to remain in the canal for a period of time sufficient for them to set. In the preferred embodiment the expandable member comprises a balloon of sufficient flexibility to conform to the shape of the uterine cavity and to enter and effectively seal the isthmus.

9 Claims, 3 Drawing Figures

MATERIAL DISPENSING APPARATUS

RELATED INVENTIONS

This invention is related to U.S. patent application Ser. No. 713,294, filed Aug. 10, 1976, entitled IMPROVED SINGLE STROKE DISPENSING APPARATUS, and invented by and assigned to the inventors and assignee of the present invention. Said application Ser. No. 713,294 is herein incorporated by reference in its entirety.

BACKGROUND OF THE INVENTION

Apparatus for dispensing materials into the Fallopian tubes of a female through non-surgical procedures have been described in a plurality of patents issued to the inventors of this invention including but not limited to U.S. Pat. No. 3,875,939, entitled SINGLE STROKE DISPENSING METHOD, issued Apr. 8, 1975.

Through the use of such dispensing apparatus, settable liquid or fluid-like materials are injected into the Fallopian tubes to occlude the canals of the tubes. The materials used for this purpose are generally fast setting, and are often sensitive to moisture, and therefore will quickly set up in the uterine cavity if not rapidly forced into the canals of the Fallopian tubes. This rapid movement of the materials is accomplished by expansion of a member which substantially fills and conforms to the shape of the uterine cavity, thus applying pressures to the materials to force them into the Fallopian tubes. It has been found that the need to use a rapidly setting material is caused, for one reason, by the undesirability of having the materials flow through the canals of the Fallopian tubes into the peritoneal cavity. Prior devices used a low viscosity, quickly setting material in an attempt to prevent this undesirable passage of materials completely through the canal of the Fallopian tube. This caused a problem because of the possibility that the rapidly setting material may begin to set up as soon as it reaches the moisture of the uterine cavity and may either remain in the cavity or cause an insufficient amount to enter the Fallopian tubes, thus causing an obvious disadvantage. This problem is overcome by the present invention which enables the use of a material with a longer setting time and, if desired, a higher viscosity. This is accomplished in the present invention by using the method and means of substantially or effectively sealing the isthmus, or entrance from the uterine cavity into the Fallopian tubes with the expandable member to prevent the materials from flowing through the Fallopian canals. The canal of the Fallopian tube is of sufficiently small diameter and the materials used are of a sufficiently high viscosity so that by thus blocking or sealing one end of the canal, the material will be held in the canal by its surface tension, much as closing one end of a soda straw will hold liquids within the straw.

SUMMARY OF THE INVENTION

This invention is directed to apparatus for dispensing materials into the canals of the Fallopian tubes of a female and to apparatus and method for assuring that the dispensed materials do not flow through the canals of the Fallopian tubes into the peritoneal cavity. More specifically, the apparatus and method is directed to introducing a predetermined amount of fluid-like, settable materials into the canals of the Fallopian tubes of a female from the uterine cavity of a female. The primary details of the apparatus are described in U.S. application Ser. No. 713,294 cited above, and incorporated by reference herein. That apparatus has an elongated probe having a forward end carrying an expandable balloon-like assembly. A dispensing housing having an actuator is used to expand the balloon assembly and to discharge the materials into the uterine cavity. The dispenser has a first drive assembly operable to initially partially expand the balloon-like assembly to form a seal and hold structure in the lower portion of the uterine cavity. Continued movement of the actuator causes discharge of the material into the uterine cavity above the partially expanded balloon-like assembly. As the actuator continues to move, the balloon assembly expands to substantially conform to and fully displace the uterine cavity and thus force the materials into the Fallopian tubes. The sequence of events is accomplished by actuation of a control actuator by an operator who moves the actuator from one position to another.

The highly flexible balloon-like member will not only conform to the shape of the uterine cavity, but will actually fill and conform to the shape of the individual isthmus of each Fallopian tube, thus effectively or substantially sealing the isthmus. By holding the control mechanism in the fully actuated position, the operator may seal the entrance to the Fallopian tubes for as long as necessary for the material to set within the canals of the Fallopian tubes. After the desired holding time, the operator may then extract the control mechanism to deflate the ballon-like member and extract the device from the body.

IN THE DRAWINGS

DESCRIPTION OF THE PREFERRED EMBODIMENT

Figure 1:
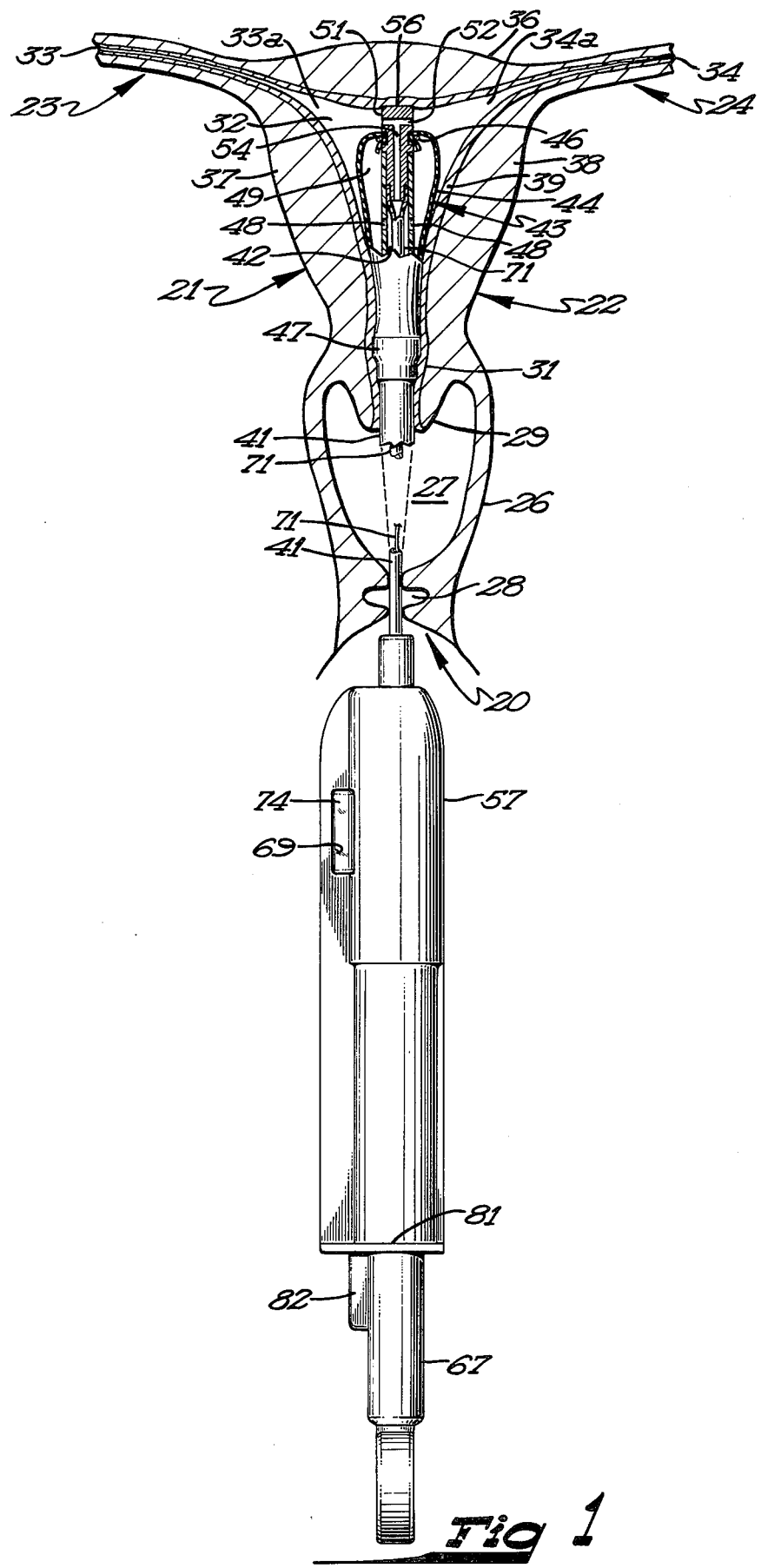
FIG. 1 is a foreshortened sectional view of a reproductive system of a female accomodating the dispensing instrument of the apparatus and method of this invention for dispensing fluids into the Fallopian tubes.

Referring to the drawings, there is shown in FIG. 1 the dispensing apparatus of this invention indicated generally at 20, the apparatus having its probe located in the uterine cavity of a female. The female reproductive system shown generally at 21 includes a uterus 22 joined to a pair of Fallopian tubes 23 and 24. The lower part of uterus 22 is integral with an elongated vagina 26. Vagina 26 has a vaginal cavity 27 including an opening or entrance 28. The opposite end of the vaginal cavity 27 is in communication with cervix 29 which in turn has a cervical opening 31 providing a passage from the vaginal cavity 27 to the uterine cavity 32. Fallopian tubes 23 and 24 open, or have entrances 33a and 34a to opposite sides of the upper part of uterine cavity 32. A uterus such as 22 is a generally pear-shaped, thick-walled, hollow organ situated between the bladder and the rectum. It is well known that the uteri of females may vary greatly in size and shape, wall thickness, wall strength, and sensitivity to pain. Therefore, the depiction in FIG. 1 of uterine cavity 32 as being triangular in shape is merely a generalization for the purposes of this disclosure.

Figure 2:
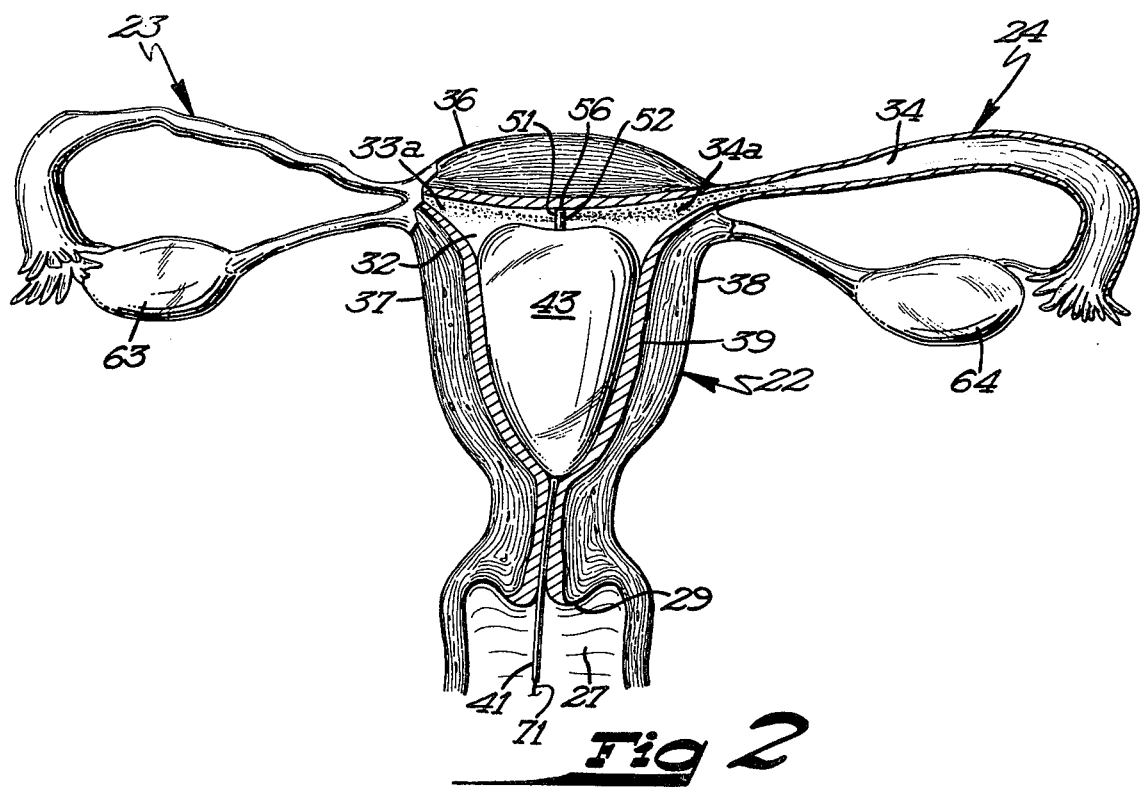
FIG. 2 is a view of the reproductive system of a female with the uterus and one Fallopian tube shown in section, and with a portion of the apparatus of this invention shown in initial fluid dispensing and expansion stage.
Figure 3:
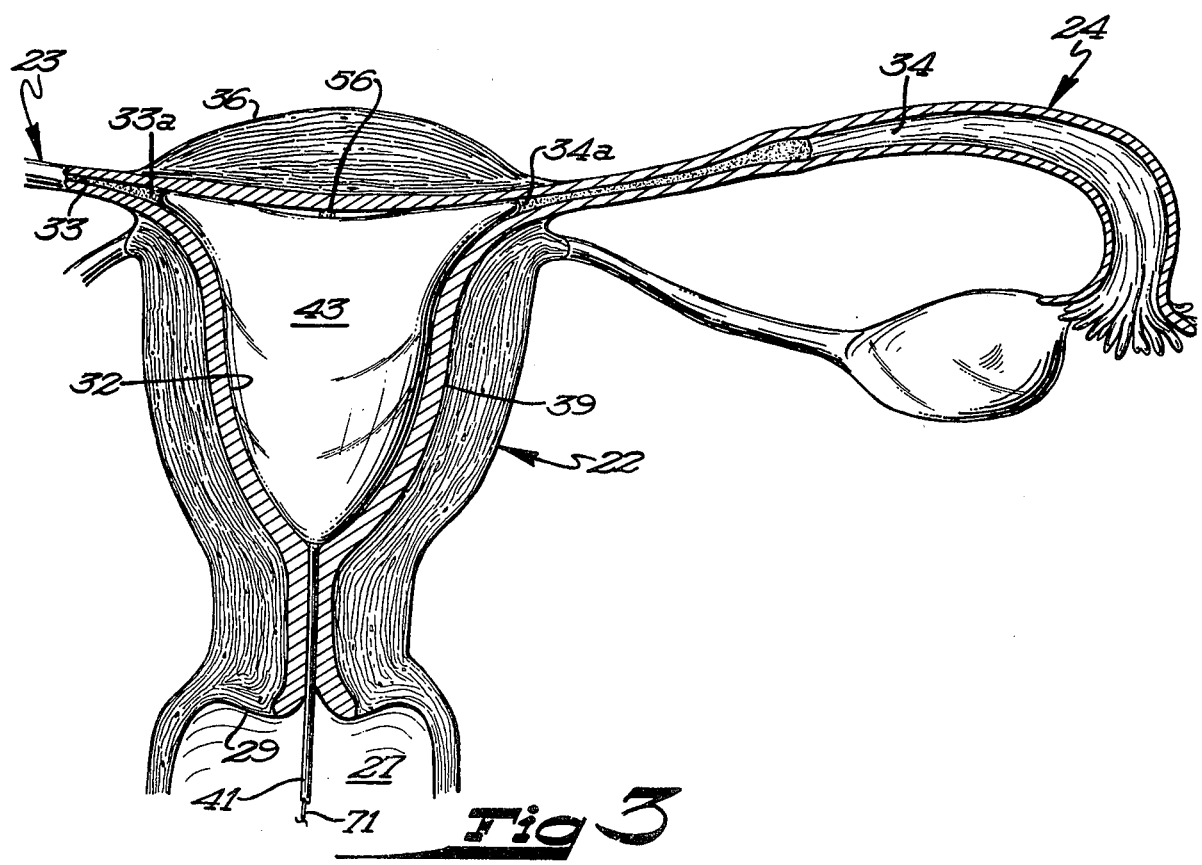
FIG. 3 is a view of the sectioned uterus and Fallopian tube showing the expandable member of the apparatus of this invention in its sealing relationship to the Fallopian tubes with the materials in the canal of the tubes.

Fallopian tubes 23 and 24 are paired, trumpet-shaped muscular members approximately 12 cm in length that extend from the superior angles of uterine cavity 32 to the female ovaries (shown in FIGS. 2 and 3). Outlets or entrances 33a and 34a of canals 33 and 34, respectively, can vary in position relative to the uterine cavity and relative to each other. Entrances 33a and 34a, referred to as the isthmus of the Fallopian tube, are most often symmetrically opposite each other, as shown in FIG. 1, and their position and proximity are principally related to the size and configuration of the uterus. It is well known that the size of canals 33 and 34 and the size of outlets 33a and 34a will vary from female to female.

Fallopian tubes are divided into isthmus, intramural, and ampullary sections. Canals or intramural sections 33 and 34 provide passages for the movement of ova from the ovaries to the uterine cavity 32, as well as the movement of sperm from the uterine cavity toward the ovaries. The intramural or canal sections of the Fallopian tubes traverse the uterine wall generally in a more or less straight fashion, but they may have a tortuous course in some females. The walls of the Fallopian tubes consist of three layers including the serosal layer, the muscular layer, and the mucosal lining.

In FIG. 1, uterus 22 is shown as having a top wall or fundus 36 and side walls 37 and 38 which surround the uterine cavity 32. The inside of fundus 36 and the inside of side walls 37 and 38 have a lining or membrane 39 which is periodically sloughed off in the normal cycle of the female.

The placement of a desired fluid into the Fallopian tubes of a female may cause either the opening or closing of the tubes to either facilitate or prevent pregnancy. Apparatus for non-surgically dispensing the desired fluid and ensuring that it enters both Fallopian tubes, such as that described in prior art patents by the inventors of this invention, including U.S. Pat. No. 3,875,939 and U.S. patent application Ser. No. 713,294, which have been incorporated by reference herein, must be able to function within the physical parameters defined above and to operate safely and surely in the uterine cavity regardless of its size or shape.

Referring again to FIG. 1, it is disclosed that a dispensing instrument 20 has an elongated probe or tubular member 41 with a length sufficient to pass through the vaginal cavity 27 and into the uterine cavity 32. In FIG. 1, the upper portion of probe 41 has been enlarged, for purposes of clarity of the drawings. Member 41 has a longitudinal passage 42 extending throughout its length. A balloon assembly, indicated generally at 43, is mounted on the upper or outer end of member 41. Balloon assembly 43 has a flexible and expandable sleeve member 44 surrounding the upper end of probe 41. A fastener 46, such as a collar or thread, provides the attachment of sleeve or sheath 44 to probe 41. Another fastener 47 attaches the opposite end of sleeve 44 to probe 41. Probe 41 has a plurality of openings 48 which provide communication between passage 42 and a chamber 49 within sleeve member 44. Sleeve member 44 may be a tubular sheet member of soft and relaxed, flexible and elastic material, such as rubber or plastic, that expands with minimum tension. Preferably, the material used for member 44 has a low surface tension which allows uniform expansion under relatively low pressure. Member 44 will thus expand to fully displace uterine cavity 32 and conform to the shape of the uterine cavity without applying extreme pressures to localized portions of walls 37 and 38 or fundus 36. Through its extreme flexibility, member 44 will also expand into and conform to the shape of isthmus 33a and isthmus 34a. This will substantially or effectively seal each isthums.

The upper or outer end of probe 41 is closed with a head 51. Head 51 has a transverse passage 52 opened to opposite sides of head 51. An elongated tube 71 is secured to head 51 and extends the length of probe 41. Tube 71, the upper portion of which has been expanded in the drawings for purposes of clarity, has a passage 54 for carrying a settable fluid-like material to the transverse passage 52 which in turn directs the material in opposite directions to create two portions in the upper section of uterine cavity 32. Head 51 has a cap 56 having a top surface or wall adapted to engage fundus 36. Cap 56 faces passage 52 from the inner wall of fundus 36.

Probe 41 is connected to a housing or body 57 which carries a cavity 69 for receiving a fluid container such as 74. A single stroke actuator 67 is connected to housing 57 to both control the expansion of balloon assembly 43 and the dispensing of fluid from container 74 through transverse passage 52. In operation of the apparatus of FIG. 1 the operator places probe 41 within uterus 22 such that cap 56 comes in contact with the fundus 36. He then depresses actuator 67 which, in a manner fully described in U.S. patent application Ser. No. 713,294, causes automatic dispensing of the materials from ampulla 74 through probe 41 and channel 52, while at the same time, causing the expansion of balloon member 43 to block the lower end of uterine cavity 32 and eventually force the dispensed materials into canals 33 and 34 of Fallopian tubes 23 and 24.

Referring now to FIG. 2, there is again shown uterus 22 with its cavity 32 and Fallopian tubes 23 and 24. The location of ovaries 63 and 64 at their respective ends of Fallopian tubes 23 and 24 are added to FIG. 2. These are located in the peritoneal cavity of the female body.

Further referring to FIG. 2, it can be seen that balloon member 43 has been expanded to block the lower end of uterine cavity 32 and that the materials are being dispensed. Also shown is a section of Fallopian tube 24 including its canal 34 and its isthmus 34a. Also shown is Fallopian tube 23 with its isthmus 33a, and though not shown in section, Fallopian tube 23 has its canal 33.

From FIG. 2, it can be seen that canals 34 and 33 lead directly to the peritoneal cavities containing ovaries 63 and 64, and as has been stated above it is undesirable to have the dispensed material reach these cavities.

In FIG. 3, can be seen the final stage of the apparatus and method of this invention wherein balloon or expandable member 43 has reached its full expansion and has conformed to the shape of the uterine cavity as well as conforming to and substantially sealing isthmus 33a and isthmus 34a. This sealing of the entrances to the canals of Fallopian tubes 23 and 24 causes the materials to be held in canals 33 and 34 much in the way that fluid can be lifted by a glass tube by holding a finger over one end of the tube. Therefore, the operator need only hold actuator 67 in its actuated position for a period of time long enough for the material to set, before releasing actuator 67, thus deflating expandable member 43 enabling the removal of probe 41 from the female.

From the apparatus and method described above, it is apparent that a material for occluding the Fallopian tubes can be used which has a longer setting period than materials which cannot be used by any means which causes the materials to stand in the canals of the Fallopian tubes without flowing through the canals into the peritoneal cavity. It is also apparent that what has been described above is the preferred embodiment and that similar embodiments could be used to accomplish the same purpose without departing from the spirit and scope of this invention.

What is claimed is:

1. Apparatus for dispensing and holding materials in the Fallopian tubes of a female comprising:
    first means for dispensing materials into the uterine cavity;
    second means for moving dispensed materials from the uterine cavity into the canals of the Fallopian tubes; and
    third means for effectively sealing the entrance to the canals of the Fallopian tubes for holding the dispensed materials within the canals.

2. The apparatus of claim 1 in which said third means includes:
    control means for effectively sealing the entrances to the canals of the Fallopian tubes for a selectable period of time.

3. In an apparatus for moving materials into the Fallopian tubes of a female, the improvement comprising:
    first means for dispensing materials into the uterine cavity;
    second means for forcing dispensed materials from the uterine cavity into the Fallopian tubes;
    control means;
    means connecting the control means to the first and second means; and
    the control means being selectively operable for holding the second means in substantial sealing relationship to the uterine entrances to the Fallopian tubes to hold the dispensed materials within the Fallopian tubes.

4. The apparatus of claim 3 in which the second means comprises:
    an expandable, flexible sheath means;
    and the control means includes means for sequentially expanding the sheath means to block the entrance to the uterine cavity, further expanding the sheath means to force dispensed materials into the Fallopian tubes and to substantially fill and block the uterine entrances to the Fallopian tubes, and for holding the expanded sheath means in substantial blocking relationship to the uterine entrances to the Fallopian tubes for a desired period of time.

5. The apparatus of claim 4 in which the sheath means comprises:
    a balloon of highly flexible and expandable material.

6. In apparatus for dispensing fluid-like materials into the Fallopian tubes of a female, including means for dispensing fluid-like materials into the uterine cavity of the female, means for expanding within the uterine cavity for moving the dispensed materials from the uterine cavity into the canals of the Fallopian tubes, and means for controlling the means for dispensing and the means for expanding, the improvement comprising:
    means within the control means for selectively holding the means for expansion in effective sealing relationship with the isthmus of each Fallopian tube.

7. The apparatus of claim 6 in which the means for expanding comprises: a balloon of sufficient flexibility and expandability to conform to the shape of and effectively seal the isthmus of a Fallopian tube.

8. The improved method of dispensing settable materials into the canals of Fallopian tubes of a female comprising the steps of:
    (a) dispensing the materials into the uterine cavity;
    (b) moving dispensed materials from the uterine cavity into the canals of the Fallopian tubes; and
    (c) holding the dispensed materials in the canals by substantially sealing the isthmus of the Fallopian tubes for a time sufficient for the materials to set.

9. The method of claim 8 in which step (c) comprises the step of:
    expanding a flexible member to enter and substantially conform to the shape of the isthmus, to effectively seal the isthmus.

* * * * *